United States Patent
Deng

(10) Patent No.: US 10,330,605 B2
(45) Date of Patent: Jun. 25, 2019

(54) METHOD OF TESTING THE COLOR QUALITY OF A COLORED GEMSTONE

(71) Applicant: Wenshuai Deng, Hunan (CN)

(72) Inventor: Wenshuai Deng, Hunan (CN)

( * ) Notice: Subject to any disclaimer, the term of this patent is extended or adjusted under 35 U.S.C. 154(b) by 0 days.

(21) Appl. No.: 15/869,058

(22) Filed: Jan. 12, 2018

(65) Prior Publication Data

US 2018/0136141 A1 May 17, 2018

Related U.S. Application Data

(63) Continuation of application No. PCT/CN2015/085476, filed on Jul. 29, 2015.

(51) Int. Cl.
*G01N 21/87* (2006.01)
*G01J 3/52* (2006.01)
*G01N 21/29* (2006.01)

(52) U.S. Cl.
CPC ............ *G01N 21/87* (2013.01); *G01J 3/52* (2013.01); *G01N 21/293* (2013.01)

(58) Field of Classification Search
CPC ...... G01N 21/87; G01N 21/33; G01N 21/293; G01N 21/255; G01N 33/381
See application file for complete search history.

(56) References Cited

U.S. PATENT DOCUMENTS

| | | | |
|---|---|---|---|
| 4,527,895 A | 7/1985 | Rubin | |
| 7,388,656 B2 | 6/2008 | Liu | |
| 8,046,274 B2 | 10/2011 | Sevdermish | |
| 2005/0149369 A1 | 7/2005 | Sevdermish | |
| 2008/0204705 A1 | 8/2008 | Liu | |
| 2015/0124273 A1 | 5/2015 | Komatsubara | |

FOREIGN PATENT DOCUMENTS

| | | |
|---|---|---|
| CN | 103196843 | 7/2013 |
| JP | 1-313723 A | 12/1989 |
| JP | 2005-516193 A | 6/2005 |
| JP | 2007-178424 A | 7/2007 |

*Primary Examiner* — Maurice C Smith
(74) *Attorney, Agent, or Firm* — Winston Hsu

(57) ABSTRACT

A method of testing the color quality of a colored gemstone is disclosed, taking the gem color as an entirety visually composed of different color components, whose total amount of color components is constant, so as to calculate hue-purity, color-strength and relative chromaticity of the gem color to test the color quality. The method comprises the following steps: (1) determining blackness, chromaticness, and hue of the gem color; (2) calculating the hue-purity, color-strength and relative chromaticity in accordance with the blackness, chromaticness, and hue; (3) finding a matching color in a pre-established standard color library for this specific gemstone according to the hue-purity, color-strength and relative chromaticity calculated in step (2), and use the name of the matching color to indicate the gem color and color quality.

15 Claims, No Drawings

METHOD OF TESTING THE COLOR QUALITY OF A COLORED GEMSTONE

CROSS REFERENCE TO RELATED APPLICATIONS

This application is a continuation application of PCT/CN2015/085476, filed on Jul. 29, 2015. The contents of PCT/CN2015/085476 are all hereby incorporated by reference.

BACKGROUND OF THE INVENTION

1. Field of the Invention

This application relates to the field of gem quality testing, particularly to the method of establishing a standard color library for a colored gemstone for testing the color quality of the colored gemstone and the method of testing the color quality of a colored gemstone.

2. Description of the Related Art

Color quality has a decisive impact on gem quality and value; therefore, testing the color quality of a colored gemstone has become a top priority in testing the quality of colored gemstones. While the general color of a colored gemstone is very clear, it is often difficult to objectively test its quality, and express the results appropriately. As a matter of fact, in the gem industry, there has been no scientific testing method that is generally accepted by the industry so far.

In the traditional evaluation of color quality in the gem industry, people usually use the natural color nomenclature to express the color quality of a colored gemstone, namely, matching similarities, naming gem color and distinguishing the quality with imaginable natural color. For example, apple green is used to indicate jadeite's apple-like light green, vivid green is used to indicate jadeite's leaf-like pure green, spicy green is used to indicate jadeite's pepper-like strong green, pigeon's blood is used to indicate ruby's pigeon's blood-like vivid red, cornflower blue is used to indicate sapphire's cornflower-like pure blue, and peach pink is used to indicate tourmaline's peach-like pale pink. The natural color nomenclature not only visually depicts the typical color appearance of a colored gemstone, but also expresses almost all of the quality characteristics of gem color at the same time. It also has a strong commercial appeal, and is very convenient for understanding, communication and application. We can say that it is the most practical color quality evaluation method. To describe more specifically the color quality of a colored gemstone, people often use intuitive visual features of color such as pure-impure, strong-weak, dark-light, bright-dull, light-heavy, cold-warm and even negative-positive to express and compare the gem color. For example, "pure, strong, vivid, even" to measure the color quality of jadeite, namely, whether the hue of the color is pure or not, whether the color is strong or not, whether the color is vivid or not, and whether the color is even or not. However, the current conventional method relies on people's subjective experience, and it is difficult to give clear explanations and specifications with prior arts, therefore, it is considered to be an informal quality evaluation method by many gem testing agencies, and it has not been really used in scientific testing of the color quality of colored gemstones. In the gemstone report of GemResearch Swisslab (GRS), the natural color nomenclature is used to indicate the quality of gem color, for example, "pigeon's blood" is used to indicate the best quality red of ruby, but there is no word about the corresponding test basis of "pigeon's blood" in the report, "pigeon's blood" is only remarked as a trade name rather than an objective test conclusion, that is to say, GRS totally relies on an inspector's subjective experience to judge whether the color of a ruby is "pigeon's blood" or not.

Prior arts for testing the color quality of colored gemstones were all developed on the basis of the theory of the three elements of color (namely, using the three basic psychological attributes of color—hue, lightness and chroma—to systematically describe the color). For example, the three elements of color (hue, value and chroma) in the Munsell nomenclature HV/C are used as quality testing indexes (there may be different terminology in practical applications) to identify, classify and describe the color quality of colored gemstones. There is a comprehensive introduction in the (Comparison of Internationally Popular Grading & Appraisal Systems of Coloured Gemstones and Its Clues for Setting up a New System published by Luo Xiang-lan, Qiu Zhi-li, Li Liu-fen, Wei Qiao-kun, Li Zhi-wei. Beijing, Journal of Gems and Gemology, 2010, the first issue). There are mainly three methods: GemSet Colorimetry, GemDialogue Colorimetry (U.S. Pat. No. 4,527,895) and CIE Spectrophotometric Colorimetry:

1. GemSet Colorimetry

GemSet is a plastic standard stone colorimetric system developed by the Gemological Institute of America (GIA) on the basis of the Munsell Color System to be specifically used for color quality grading of colored gemstones. It basically copies the study routine of the Munsell Color System to identify and classify the gem color, and it only replaces Munsell value with tone and Munsell chroma with saturation. GemSet identifies the color quality of colored gemstones by determining the hue, tone and saturation of gem color through the comparison of plastic standard stones whose three elements of color have been calibrated, and it divides and indicates the quality grading of the gem color according to a preset color quality grading table.

The disadvantages of this method are that it is too professional, its specific color terminology, measurement and quality expression do not comply with market habits of the gem industry and people's habits of language and thinking. For example, the so-called tone in this method (in fact, Munsell value) is not always the greater the better or the smaller the better, it should be appropriate; and the so-called "vslbG", "vstbG" hue, and quality expression of "fancy vivid purple pink" are all hard for people to generate specific color impression and measurement standards, which is not conducive to understanding, communication and grasp. In addition, mix of concepts of color in this system can easily cause difficulties in understanding. For example, there is no necessarily logical relationship among gray, brown, strong and vivid which are used to indicate the quality of saturation, and its manner of using multiple color characteristics with different indicating objects to express saturation is neither consistent with professional norms of the Munsell Color System nor in line with the color perception habits of the individual. The so-called saturation level symbol (Munsell chroma is reduced to 6 grades by GemSet) is also very easy to be confused with Munsell chroma. In addition, this system has many other problems: large subjective factors, colors covered by standard samples are limited, plastic standard samples are prone to aging, a huge standard sample system, inconvenient to use and operate, etc. Because of the above defects, GIA also developed the GIASquare system on the basis of GemSet according to color digital encoding technology. However, the testing method and procedures are too specialized and complex and completely out of the actual market, so it is not practical.

2. GemDialogue Colorimetry (U.S. Pat. No. 4,527,895)

GemDialogue is a color atlas colorimetric system developed by Howard Rubin on the basis of the Munsell Color System to be specifically used for color quality evaluation of colored gemstones, which is popular in the current international gem quality testing field and adopted and recommended by the American Gem Trade Association (AGTA). The system consists of 21 separate color charts and 3 color masks: the 21 transparent color charts represent 21 specific colors, each of the color charts is divided into 100, 90, . . . 10 from high to low, that is, 10 saturation zones in total; the 3 color masks are respectively opaque black/white, transparent gray and transparent brown, each of the color masks also be divided into 10 zones so as to be superimposed with the color charts to match the color of colored gemstones. GemDialogue simulates and matches the color of colored gemstones by superimposing color charts and color masks, so as to use the color and saturation zone of the color chart, the color and the degree of masking to test the color quality of colored gemstones. And it indicates the color of colored gemstones and divides quality grades according to the particular format "color chart, saturation zone/degree of masking, color mask" and a preset color quality grading table.

Although GemDialogue was developed on the basis of the Munsell Color System, its concepts of color can never be confused with the three elements of color in the Munsell nomenclature HV/C, its color hue obtained by superimposing color chart and color mask is comprehensively decided by the hue of the color chart and the color mask, and the chroma and lightness are comprehensively decided by the chroma and lightness of the color chart and the color mask. GemDialogue actually uses the characteristic parameters of the GemDialogue color atlas, rather than properties of the gem color itself to test and indicate the color quality of colored gemstones. For the mass market, its additional conceptual terms, measurement and colorimetric manner are in fact more professional and uncommon than the three elements of color, which are not only inconsistent with the gem industry tradition and the color perception habits of the individual, but also can be easily confused with the three elements of color, thus it has a high demand on the user's professional knowledge and it is not very practical. Besides, it is difficult for people to clearly explain exactly what the so-called color chart or mark is, what the saturation zone of color chart or degree of masking is, and its relationship with the color of gems, if they have not been specially trained and have not read the instructions or color atlas. It is also difficult to accurately understand and grasp what color the color notation such as B1G, B2G, G2B, R2O, O2Y as well as "P2B 100/80 black" indicates, what it is like, what the relationship between the color notation and gem color is, and can never be naturally linked to the specific gem color. What's more, the system also has problems such as big color difference between different color charts and low measurement accuracy. And it tests the color quality through superimposing color charts and marks which are independent and unrelated in the form but mutually interfere with each other in substance (color characteristics such as the three elements of color), this is complex to operate and there may be some combinations of different color charts and marks which have the same or similar color, thus resulting in inaccurate test results. In addition, in this system, the higher degree of the color marks, the lower the color quality, such an evaluation method is also in conflict with people's thinking habits.

3. CIE Spectrophotometric Colorimetry

CIE Spectrophotometric Colorimetry is an absolutely physical and professional color research method, based on the principle of mixing the three primary colors to obtain any color, and it indicates the color by measuring the spectral tristimulus values of color and CIE chromaticity coordinates. It is usually used for research on colored light. However, in fact, it is not suitable for the testing and indication of the object color of colored gemstones, as it is far too professional, abstract, complex, cumbersome and expensive. Taking China's current standard of "Jadeite Grading" as an example, the standard uses a spectrophotometer to measure the spectral reflectance or transmittance of jadeite color to obtain spectral tristimulus values, dominant wavelength and purity of excitation (Pe) of the corresponding colored light: the hue is simulated with dominant wavelength and the chroma is simulated with purity of excitation so as to test the color quality of jadeite. However, dominant wavelength and purity of excitation in CIE describe the objective attributes of colored light, while hue and chroma in the three elements of color describe the psychological attributes of color; there is no strictly equal correspondence between the two. In this standard, the objective attributes of colored light are taken as equivalent to the psychological attributes of color so as to carry out the inspection, this is theoretically not rigorous enough. And the luminance factor (can be equivalent to causing people's lightness perception) measured using the spectrophotometer cannot be used to simulate the lightness of jadeite color, it still requires using GemDialogue to test the so-called "lightness". However, GemDialogue cannot detect lightness, and it is not feasible to test the quality of gem color by the replacement of concepts between different color systems. What's more, in practice, the standard uses different lighting and measurement methods for different jadeites (for example, for common jadeite, spectral reflectance is measured using reflective lighting; and for dark green jadeite, spectral transmittance is measured using transmitted lighting) so that the so-called chroma test result can match people's sense of color strength, this is obviously not objective.

In addition to the above three methods, people also directly use the standard color atlas of the Munsell Color System for visual comparison of the three elements of gem color to test the color quality, for example, the Gem and Jewelry Institute of Thailand (GIT). However, even the three elements of color are unfamiliar to the gem industry, the reason is that the gem industry is a mass industry, the vast majority of people do not have a professional background in color theory; besides, the measurement method for the three elements of color in the HV/C nomenclature places emphasis more on physical properties (therefore in chromatics, this research method is referred to Psychophysics, and the three elements of color are named as psychophysical quantity), it is too professional, so it is difficult for ordinary people to naturally understand the specific meaning represented by the abstract value artificially defined in this particular measurement method. For example, in the gem industry, most people do not know that in the HV/C nomenclature, different hue or different lightness of the same hue has different chroma range, nor do they know how many chroma values there are in each hue and each lightness, or what the maximum chroma is; and such hues and color notations as 7.5Y8/6, 5Y9/6, 5Y8/8 and 2.5GY9/12 are also difficult to arouse people's natural color association to form specific color impression and color concepts. In fact, the color characteristics described by the three elements of color are very similar to the quality characteristics in people's common experience, for example, whether a hue is pure or not, how strong or how weak a color is, and how vivid a color is. Therefore, using the specious three elements of color as the quality indexes is not only impractical for clearly explaining the traditional practical experience of the gem industry and quality characteristics of gem color, but is also very likely to cause confusion in concepts and difficulty in understanding.

Therefore, how to test and indicate the color quality of a colored gemstone in a scientific and reasonable way has always been the most important issue in the field of international gem quality testing.

SUMMARY OF THE INVENTION

This application aims at providing a method of testing the color quality of a colored gemstone, which is more in line with the color perception habits of the individual, more in line with the traditional practices of the gem industry and more feasible. As we know, prior arts have many problems, for example, they are too professional, complex, difficult to explain clearly, identify objectively, reflect intuitively and indicate commonly the color quality of colored gemstones, and cannot meet the actual demand of the gem market. Therefore, the application is intended to show a way to completely solve these problems.

To achieve the above purpose, the following technical solutions are used in this application:

A method of establishing a standard color library for a colored gemstone for testing the color quality of the colored gemstone, taking the color of the colored gemstone as an entirety visually composed of different color components, whose total amount of color components is constant, so as to calculate hue-purity, color-strength and relative chromaticity of said color to establish said standard color library for said colored gemstone, the steps are as follows:

(1) collecting a plurality of colored gemstone samples as a training set;

(2) determining blackness, chromaticness, and hue of the color of said colored gemstone samples in said training set in a standard environment, wherein said color components include colored components and a white visual component, wherein said colored components include a black visual component and all chromatic visual components, wherein said blackness is the percentage content of said black visual component in said color of said colored gemstone, wherein said chromaticness is the percentage content of said chromatic visual components in said color of said colored gemstone;

(3) calculating said hue-purity, said color-strength and said relative chromaticity of said color of said colored gemstone samples according to said blackness, said chromaticness and said hue:

wherein said hue-purity represents the degree of purity or impurity and the offset color of said hue of said color of said colored gemstone calculated on the basis of one of four psychological primary colors and transitional intermediate colors; wherein said four psychological primary colors are red, green, yellow and blue, wherein red and yellow, red and blue, yellow and green, green and blue are not opposed, there is a transitional intermediate color between two psychological primary colors which are not opposed; wherein said transitional intermediate colors are orange which between yellow and red, and purple which between red and blue; when red and yellow, or, red and blue are detected in the color of colored gemstone samples, using one of the following two calculation methods: (a), hue-purity is x % the secondary psychological primary color to the main psychological primary color; and (b), hue-purity is y % the main psychological primary color to the transitional intermediate color; when green and blue, or, yellow and green are detected in the color of colored gemstone samples, the hue-purity is x % the secondary psychological primary color to the main psychological primary color; wherein x % is the percentage proportion of the secondary psychological primary color in the hue, y % is half of the difference between the percentage proportion of the main psychological primary color in the hue and the percentage proportion of the secondary psychological primary color in the hue;

wherein: said main psychological primary color means the psychological primary color whose percentage proportion in said hue is more than 50%, and said secondary psychological primary color means the psychological primary color whose percentage proportion in said hue is less than 50%; when the percentage proportions of both psychological primary colors in said hue are 50%, then either of the psychological primary colors can be taken as said main psychological primary color, and the other can be taken as said secondary psychological primary color;

wherein said color-strength is as follows: color-strength=blackness+chromaticness;

wherein said relative chromaticity is as follows: relative chromaticity=chromaticness/color-strength; and (4) identifying, classifying, quantifying and defining the specific color represented by each colored gemstone sample in said training set according to said hue-purity, said color-strength and said relative chromaticity calculated in step (3) to get said standard color library for said colored gemstone.

According to the Opponent Color Theory, the human visual system consists of two achromatic colors (black versus white), four psychological primary colors (red versus green, yellow versus blue), a total of six basic color visions which are inherent and not similar to each other, any color in color perception can be similar to two achromatic colors (black and white), and can be similar to at most two non-opposing psychological primary colors. In the above technical solution, in the four psychological primary colors (red, green, yellow and blue), red and green are opposed, yellow and blue are opposed, that is to say, red and yellow, red and blue, yellow and green, green and blue are not opposed. There is a transitional intermediate color between two psychological primary colors which are not opposed, for example, the transitional intermediate color between yellow and red is orange, and the transitional intermediate color between red and blue is purple.

Preferably, said blackness, said chromaticness and said hue are directly measured by using a color scan of the Natural Color System or determined by visual comparison between said colored gemstone samples and standard color cards of the Natural Color System.

Preferably, said blackness and said chromaticness are respectively equivalent to value B and value C determined by using the Ostwald Color System, and said hue is determined by using the Natural Color System.

Preferably, said standard environment is selected from one of a group composed of D50, D55 and D65 standard illumination environments.

Preferably, said identifying, classifying, quantifying and defining in said step (4) also includes using natural color nomenclature or said hue to name specific colors represented by said colored gemstone samples.

In establishing the standard color library, select color samples of the colored gemstone widely recognized by the market to establish the training set for conventional gem colors that may be named by natural color nomenclature such as pigeon's blood, cornflower blue, emerald green, vivid green, peach pink, claret red, golden yellow etc., give precise definitions to the specific colors represented by the colored gemstone samples according to the hue-purity, color-strength and relative chromaticity quantified by this application; in the established standard color library, natural color nomenclature can be used to name and indicate the color and color quality of the colored gemstones. However, colors with low market value or no precise statement can be directly classified and named by the hue according to the obtained hue-purity in the established standard color library, the specific naming method can be "the secondary psychological primary color+"ish"+the main psychological primary color", for example, the color with hue-purity of 30% yellow to green can be named yellowish green. When the hue-purity of the color of a colored gemstone is indicated based on the transitional intermediate color, the naming method can be "the main psychological primary color+"ish"+the transitional intermediate color", for example, the color with hue-purity of 5% blue to purple can be named bluish purple, the color with hue-purity of 9% red to purple can be named reddish purple, and the color with hue-purity of 10% red to orange can be named reddish orange. In naming gem colors, it is unnecessary to include all hue-purity, color-strength, relative chromaticity and even characteristics of the color such as amount, shape, uniformity, diversity, etc.

A method of testing the color quality of a colored gemstone, taking the color of the colored gemstone as an entirety visually composed of different color components, whose total amount of color components is constant, so as to calculate hue-purity, color-strength and relative chromaticity of said color to test said color quality of said colored gemstone, the steps are as follows:

(1) determining blackness, chromaticness, and hue of the color of said colored gemstone to be measured in a standard environment, wherein said color components include colored components and a white visual component, wherein said colored components include a black visual component and all chromatic visual components, wherein said blackness is the percentage content of said black visual component in said color of said colored gemstone, wherein said chromaticness is the percentage content of said chromatic visual components in said color of said colored gemstone;

(2) calculating said hue-purity, said color-strength and said relative chromaticity of said color of said colored gemstone to be tested according to said blackness, said chromaticness and said hue:

wherein said hue-purity represents the degree of purity or impurity and the offset color of said hue of said color of said colored gemstone calculated on the basis of one of four psychological primary colors and transitional intermediate colors; wherein said four psychological primary colors are red, green, yellow and blue, wherein red and yellow, red and blue, yellow and green, green and blue are not opposed, there is a transitional intermediate color between two psychological primary colors which are not opposed; wherein said transitional intermediate colors are orange which between yellow and red, and purple which between red and blue; when red and yellow, or, red and blue are detected in the color of colored gemstone samples, using one of the following two calculation methods: (a), hue-purity is x % the secondary psychological primary color to the main psychological primary color; and (b), hue-purity is y % the main psychological primary color to the transitional intermediate color; when green and blue, or, yellow and green are detected in the color of colored gemstone samples, the hue-purity is x % the secondary psychological primary color to the main psychological primary color; wherein x % is the percentage proportion of the secondary psychological primary color in the hue, y % is half of the difference between the percentage proportion of the main psychological primary color in the hue and the percentage proportion of the secondary psychological primary color in the hue;

wherein: said main psychological primary color means the psychological primary color whose percentage proportion in said hue is more than 50%, and said secondary psychological primary color means the psychological primary color whose percentage proportion in said hue is less than 50%; when the percentage proportions of both psychological primary colors in said hue are 50%, then either of the psychological primary colors can be taken as said main psychological primary color, and the other can be taken as said secondary psychological primary color;

wherein said color-strength is as follows: color-strength=blackness+chromaticness;

wherein said relative chromaticity is as follows: relative chromaticity=chromaticness/color-strength; and (3) finding a matching color in a pre-established standard color library for this specific colored gemstone according to the said hue-purity, said color-strength and said relative chromaticity calculated in step (2), and using the name of the matching color to indicate said color and said color quality of said colored gemstone to be tested.

Preferably, said blackness, said chromaticness and said hue are directly measured by using a color scan of the Natural Color System or determined by visual comparison between said colored gemstone sample and standard color cards of the Natural Color System.

Preferably, said blackness and said chromaticness are respectively equivalent to value B and value C determined by using the Ostwald Color System, and said hue is determined by using the Natural Color System.

Preferably, said standard environment is selected from one of a group composed of D50, D55 and D65 standard illumination environments.

Compared with prior arts, the beneficial effects of the testing method provided in this application are as follows: Color is actually a sensation triggered by visual nerve stimulation from visible light, it not only has physical attributes such as various optical parameters like dominant wavelength and luminance factor as well as color-producing pigments, but it also has psychological attributes such as the three elements of color and the color-strength in this application. Prior arts are too dependent on the mechanical application of the existing physically professional theory such as the three elements of color (color is defined as an "objective physical quantity"), as a result, such methods of color quality testing are not so relevant to the actual market. This application is the first to introduce a psychology-based color research method into the field of gem quality testing, and pioneering the research on gem color as a purely psychological sense. Compared with the prior arts, the method laid out in this application has stronger logic regularity and measures the hue-purity, color-strength and relative chromaticity of gem color as its quality testing indexes in full accordance with people's physiological visual law. It further uses the natural color nomenclature to classify and name the color of colored gemstones, which really follows people's color perception habits, thinking habits and industry tradition to identify and indicate the color quality of colored gemstones. This is not only more scientific, reasonable, accurate, reliable, simple and efficient, but also more vivid, intuitive and easy to understand. For example, it can be used to quickly compute and calibrate the color quality of a colored gemstone by simply using a color scan of the Natural Color System to determine a color notation (the color notation includes blackness, chromaticness, and hue required by calculating the hue-purity, color-strength and relative chromaticity); all quality indexes are intuitive color characteristics of the gem color itself, and the identification and comparison can be subject to the maximum (the higher the hue-purity, color-strength and relative chromaticity, the better); it uses the inherent basic color visions in people's visual system to identify the hue-purity of the gem color, and indicates the gem color and calculates its quality indexes with the common natural color nomenclature and percentage form. People can quickly understand, master and use it without special color theory training, and it helps to popularize the market and has a significant and positive impact on the establishment of practical and feasible quality standards for colored gemstones and the promotion of healthy and orderly development for the colored gemstone market.

These and other objectives of the present invention will no doubt become obvious to those of ordinary skill in the art after reading the following detailed description of the preferred embodiment that is illustrated in the various figures and drawings.

DETAILED DESCRIPTION

The following is a further description of the application in accordance with the preferred embodiments.

Principles of the method of testing the color quality of a colored gemstone provided in this application are as follows:

The more vivid the color of a colored gemstone, the better the color quality, the method of testing the color quality of a colored gemstone provided in this application takes the color of the colored gemstone as an entirety visually composed of different color components, whose total amount of color components is constant, so as to calculate hue-purity, color-strength and relative chromaticity of the color of the colored gemstone, and test the color quality by calibrating the vividness of the gem color with the hue-purity, color-strength and relative chromaticity. Wherein, the color components include colored components and a white visual component; the colored components include a black visual component and all chromatic visual components, which is opposite to the white visual component. Wherein, hue-purity is the purity of the hue of the color of the colored gemstone; color-strength is the strength of the colored components in the color of the colored gemstone; relative chromaticity is used to describe the relative degree of purity of the chromatic visual components of colors with similar hue-purity and color-strength or the relative vividness of a color in similar colors, in which the similar hue-purity refers to the same color components contained in the hue and the percentage proportion of the contained color components are within a predetermined range, the similar color-strength refers to the color-strength within a predetermined range, the similar colors refer to the colors with similar hue-purity and color-strength. The three quality testing indexes (hue-purity, color-strength and relative chromaticity) constitute a complete color quality testing system, namely, the higher the hue-purity, color-strength and relative chromaticity of the color, the more vivid the gem color and the better the color quality.

In order to better explain concepts and measurement methods of the hue-purity, color-strength and relative chromaticity, the following is a further explanation, comparing them with the three elements of color in the HV/C nomenclature, saturation and vividness:

The hue in the three elements of color is used to describe the chromatic appearance of a color such as red, orange, yellow, green, cyan, blue and purple, etc.; while neutral colors such as black, white and gray have no hue. In the HV/C nomenclature, hue is indicated by a specific notation of the system, for example, in the Munsell Color System, 2.5G indicates a yellowish green, 10BG indicates a bluish green, and 5PB indicates a blue, etc. However, in this application, hue-purity focuses on the identification of relative difference of similar hues (refer to the same color components contained in the hue and the percentage proportions of the contained color components are within a predetermined range), and the quality of the color of a colored gemstone is tested and indicated by calculating the purity or impurity and the offset color of the hue of the color of the colored gemstone with a specific color as a reference, for example, whether the red of ruby is pure or impure (with or without an offset color), yellowish or bluish, and how pure or impure the hue is. The meanings of the two are not the same, and thus the measurements and indications are also different.

In the three elements of color, lightness is used to describe the lightness or darkness of a color. Modern color order systems usually set the lightness of pure black to 0, the lightness of pure white to 10, and divide it into a total of 11 levels according to perceived equidistance, the greater the lightness, the brighter the color, the smaller the lightness, the darker the color. Chroma is used to describe the intensity of the chromatic stimulus of a color, and neutral colors such as black, white and gray have no chroma. In the HV/C nomenclature, chroma is measured as the departure degree of a color from the neutral color of the same lightness according to perceived equidistance. The maximum intensity of the chromatic stimulus of colors with different hues (namely, the intensity of the chromatic stimulus of pure chromatic colors with different hues) and the maximum intensity of the chromatic stimulus of colors with the same hue but different lightness are different, so the chroma range and maximum chroma of each hue and lightness are different. For example, in the Munsell Color System, the maximum chroma of most hues is more than a dozen and some can reach twenty. In the method presented in this application, color-strength is a concept of color in psychology generated by the concept of concentration in analogy physics, which is used to describe the intuitive characteristic of strong or weak gem color. It only makes sense to understand and measure the color as a whole, the darker, the more colorful, the stronger, the whiter the weaker; in other words, black, gray and all chromatic colors can increase the strength of color on psychological feeling, while white will reduce the strength. Obviously, this color-strength and the chroma in the three elements of color refer to two different things, and it is significantly different from lightness. For example, in people's common sense and experience, the strength of dark blue of a sapphire which is close to black is very strong, but its lightness and chroma are very low.

Due to the color characteristics described by lightness, chroma in the HV/C nomenclature and the so-called saturation have a certain similarity with the vividness in people's common sense and experience, some research directly makes equivalent substitution between lightness, chroma, saturation and vividness, and even regards lightness, chroma and saturation as vividness. However, this is not true as a matter of fact:

Saturation in fact is a concept borrowed from physics. In physics, when solute concentration in a solution reaches the maximum, the solution is then saturated, and the maximum concentration of the solute in unit solution is then called saturation of the solute in the solution, which is essentially a concentration concept (concentration threshold or equivalent to concentration). However, in chromatics, the meaning of saturation is much more complex and not so exact. In fact, saturation is not an inherent and normative concept of color in the HV/C nomenclature; it is used to describe color characteristics because it is easy to understand and can facilitate the need of practical application to replace chroma of color, purity of colored light or concentration or purity of pigment in ideographic comparison. For example, in the TV industry, the purity of the spectral color is set as the saturation point of purity of the colored light with the same dominant wavelength, so at this time, saturation can be equivalent to the purity of colored light. Another example is that in the art industry or printing industry, saturation is used to indicate the concentration or purity of a pure pigment in a mixed pigment, so as to facilitate pigment mixing. When there is only one pure chromatic pigment excluding black, gray and white pigment in the mixed pigment, the so-called saturation can be equivalent to chroma. If however there is also a variety of chromatic pigments or when the chromatic pigment is impure, then saturation is the concentration or purity in common meaning and it is totally different from chroma. In practical application, unless otherwise specified, saturation usually refers specifically to the saturation of spectral color in color, and colors saturated are usually the most vivid, therefore, this can easily lead to the inertia illusion that the more saturated the color, the more vivid the color, and that saturation is vividness; this can even lead to the fallacy that saturation must be chroma, because saturation is the concept of concentration in essence, chroma is then vividness or "concentration" of the color. As a matter of fact, saturation can be equivalent to chroma in analogy concept only under certain circumstances, and it cannot directly reflect the vividness of a color.

However, from the perspective of the three elements of color, vividness is actually related to hue, lightness and chroma. Colors of different hues with the maximum chroma have different vividness; for colors of the same hue, it is not the higher the chroma, the more vivid the color. This is because vividness depends not only on chroma but also on lightness, to say it in a common way, colors with the same hue and chroma may be blackish or may be whitish, thus exhibiting different vividness. Therefore, chroma or so-called saturation cannot be equivalent to vividness or measure vividness in linearity.

Lightness also should not be confused with vividness, for any color, the closer it is to white, the greater the lightness is; lightness of pure white is the maximum but it is obviously not the most vivid. Actually, there is no direct or necessary link between lightness and vividness, and thus it is difficult to use lightness, chroma and hue, namely, the three elements of color, to clearly calibrate and reflect the vividness of a color and its variation: the greater the lightness, the brighter the color, it is whitish if it is too bright; the smaller the lightness, the darker the color, it is blackish if it is too dark, vividness of the color will be reduced if the color is whitish or blackish, and the whitish color may not be more vivid than the blackish color or the blackish color may not be more vivid than the whitish color. In other words, the linear change of lightness of colors with the same hue and chroma does not cause the corresponding linear change of vividness. In fact, the chroma or vividness can only be at the maximum level when the lightness is moderate. However, the lightness of colors of different hues with the maximum chroma (namely the appropriate lightness) is different, lightness of some hues must be greater to achieve the maximum chroma while some must be smaller to achieve the maximum chroma, which cannot be derived by simply using the exact logical relationship (it is impractical that the identification or comparison is subject to suitability). Because of this uncertain relationship, lightness in fact does not have objective significance for identification of vividness. In addition, different hues or different lightness values have different chroma ranges, and different chroma values have different lightness ranges, it is difficult for ordinary people to understand and grasp the use of the three elements of color to test and indicate the vividness of gem color.

In order to objectively reflect the varying regularity of vividness of gem color, the method of testing the color quality of a colored gemstone provided in this application is to use a psychological research method to take the color of the colored gemstone as an entirety visually composed of different color components (wherein said color components include a white visual component, a black visual component and all chromatic visual components), whose total amount of color components is constant, so as to simulate "solute" with colored components including the black visual component (Note: gray is the color presented after black is diluted, so it is no longer regarded as a mere visual component and is included in the black visual component.) and all chromatic visual components, simulate "solvent" with the white visual component and simulate "solution" with all color components to calculate the percentage content of the colored components in the color, namely, the strength of the gem color on psychological feeling. It is also a way to calculate the ratio between chromatic visual components and colored components, namely, the relative chromaticity which identifies and indicates the color quality of the colored gemstone according to the changing relationship between the chromatic visual components and the black visual component in the certain total amount of colored components. And then use the three quality indexes, the hue-purity, color-strength and relative chromaticity to calibrate the relative vividness of the gem color in similar colors. In other words, vividness is actually a concept in a relative meaning rather than in an absolute meaning, while relative chromaticity only makes sense when compared in similar colors with same or similar hue-purity and color-strength.

For colors with the same or similar hue-purity and color-strength, the greater the relative chromaticity, the higher the proportion of the chromatic visual components in the colored components, the less the proportion of the black visual component, and the more vivid the color, take ruby as an example, there are subtle differences in quality between different "pigeon's blood", "pigeon's blood" with a lower relative chromaticity appears darker because of its relatively deeper color, resulting in low vividness and quality. For colors with different hue-purity such as the purple, green, yellowish green and bluish green of jadeite, or for colors with the same or similar hue-purity but different color-strength such as the apple green, spicy green and dark green of jadeite, significant differences in hue-purity or color-strength lead to different aesthetic beauty, market diversification color aesthetic and value orientation, so it is not particularly meaningful to compare the vividness of colors by relative chromaticity, and the quality of colors can be visually indicated and differentiated by the color names quantified and defined by the hue-purity, color-strength and relative chromaticity.

The above comparison shows that, when compared to the three elements of color, the hue-purity, color-strength and relative chromaticity in this application places emphasis more on integrity and logic. However, the three elements of color are more independent of each other, each is measured by an independent method, and there is no clear logical link between them, they tend to be three separate characteristic quantities, and thus are not suitable to calculate the hue-purity, color-strength and relative chromaticity in this application. Therefore, this application uses the Natural Color System with stronger logical relationships in color based on a psychology color research method to measure the color parameters (hue, chromaticness and blackness) in order to calculate the hue-purity, color-strength and relative chromaticity.

Developed from the Opponent Color Theory by Ewald Hering, the Natural Color System (NCS) is a color order system built on the basis of people's physiological vision and describes color by using color similarity relationships. It uses purely sensual, visual similarity relationships to describe the color, so it is referred to as a psychology method, while the HV/C nomenclature using the three elements of color to describe the color is more physical. Hue, chromaticness, blackness and whiteness used to describe the color are referred to as psychological quantities so as to be distinguished from the three elements of color (psychophysical quantities). According to the Opponent Color Theory, the human visual system consists of a total of six basic color visions which are inherent and not similar to each other, namely, two achromatic colors (black versus white) and four psychological primary colors (red versus green, yellow versus blue), and any color in color perception can be similar to the two achromatic colors (black and white) and at most two non-opposing psychological primary colors. In the Natural Color System, the NCS notation S sscc-AϕϕB systematically describes the color by using the similarity relationships between color and six visual reference colors, namely, the visual components of the color in color perception: the blackness ss indicates the degree of similarity between the color and pure black, namely, the percentage content of the black visual component in color perception; the whiteness (100-ss-cc) indicates the degree of similarity between the color and pure white, namely, the percentage content of the white visual component in color perception; the chromaticness cc indicates the degree of similarity between the color and pure chromatic color with same hue, namely, the percentage content of the chromatic visual components in color perception; the percentage of chromatic visual components AϕϕB indicates the hue of the color, namely, 100-ϕϕ and ϕϕ indicate the degree of similarity between the hue and psychological primary color A and B, or the percentage proportions of the psychological primary color A and B in the chromatic visual components in color perception.

The Natural Color System quantifies the color into a constant visually composed of a black visual component, a white visual component and chromatic visual components and can be logically derived with a mathematical formula, therefore, it is very suitable for the measurement and calculation of the hue-purity, color-strength and relative chromaticity in this application: determine the blackness, chromaticness, and hue of a gem color with the NCS first, take the inherent four psychological primary colors in people's visual system (red, green, yellow and blue) as a reference, and then simply take the secondary psychological primary color and its percentage proportion in the hue as the offset color and the impurity of the hue, thus the hue-purity of the gem color can be obtained; by combining the blackness and chromaticness, the color-strength can be calculated; while relative chromaticity can be calculated by dividing chromaticness into color-strength. In addition to using the four psychological primary colors, we can also use the transitional intermediate color between two non-opposing psychological primary colors included in the hue of the gem color as a reference to calculate and indicate the hue-purity of the gem color. For example, the transitional intermediate color between yellow and red is orange (visually mixed together by the two psychological primary colors, yellow and red), its hue-purity can be indicated as y % yellow to orange, y % red to orange; and the transitional intermediate color between red and blue is purple (visually mixed together by the two psychological primary colors, red and blue), its hue-purity can be indicated as y % blue to purple, y % red to purple. When calculating the hue-purity with the transitional intermediate color as a reference, the offset color of the hue is the main psychological primary color, and the impurity degree y % is half of the difference between the percentage proportions of the two psychological primary colors in the hue. For example, when red and yellow are detected in the color of the colored gemstone samples, if red is assumed as the main psychological primary color, yellow as the secondary psychological primary color, the hue-purity can be: hue-purity=x % yellow to red, wherein x % is the percentage proportion of yellow in the hue; the hue-purity can also be: hue-purity=y % red to orange, wherein y % is half of the difference between the percentage proportion of red and the percentage proportion of yellow in the hue. What is more appropriate is that, when green and blue or yellow and green are detected in the color of colored gemstone samples, the hue-purity can be better indicated as x % the secondary psychological primary color to the main psychological primary color.

In addition to the Natural Color System, we can also use the Ostwald Color System to determine the blackness and chromaticness of the color of the colored gemstone. In this system, color is also considered a constant, visually made up of white, black and pure chromatic color (it's called full color in the system), namely, value W (the amount of white in a color)+value B (the amount of black in a color)+value C (the amount of full color in a color)=100(%). Said value B and value C are respectively equivalent to the blackness and chromaticness in this application, and the hue is still determined by using the Natural Color System.

It should be noted that the method of testing the color quality of a colored gemstone provided in this application takes the color of the colored gemstone as a purely psychological sense and uses a psychology-based research method. Therefore, the components, parameters and color-strength of gem color involved in this application are psychological attributes and visual characteristics of color, and have nothing to do with the material components (physical or chemical components), spectral components or spectral parameters of color. For example, if a reconciled pigment including red and white is uniformly mixed with green pigment, then the physical concentration of the red pigment and the green pigment will be reduced, but the color strength of the new reconciled pigment on psychological feeling will be increased, this is because the mixing of red and green pigments will cause the change of the original colored component (namely, red), such as the creation of a new black component, which is a color component in color perception and not a black pigment in material.

In order to ensure the objectivity and fairness of the test results, it is necessary to use D50, D55 or D65 standard illumination environments while conducting the color quality tests, namely, the color temperature of the illumination is 4500K~5500K (D50), 5000K~6000K (D55) or 6000K~7000K (D65), the color rendering index should be no less than 90, incidents from one side in the form of diffused light, and the illuminance formed in the observation plane should be within 1500 lx~2500 lx. Samples to be tested are placed in an opaque and non-directional reflective white backing; the surrounding color of the test environment is a non-directional reflective neutral color (e.g. white) and is undisturbed by other light or color.

The application is further illustrated by the following specific implementation embodiments:

Example 1

Jadeite is a kind of gem with rich colors. The method provided in this application is used to establish a standard color library for jadeite for testing the color quality of jadeites.

1) Collect a plurality of representative color samples of jadeite as the training set.

This implementation embodiment has collected 200 jadeite samples, the color of the samples covers green, white, yellow, red and purple, wherein green includes vivid yellowish green, vivid green, spicy green, apple green, spinach green, dark green and other common specific colors named by the market, and purple includes pinkish purple, reddish purple, bluish purple, strong purple, eggplant purple and other common specific colors.

In a D50 standard illumination environment, use a NCS color scan to determine the blackness, chromaticness, and hue of the color of the samples in the training set. The test results of all colors of samples are shown in Table 1 (due to the huge amount of data, Table 1 only lists the test results of some typical colors).

TABLE 1

| | | Color Parameters | | |
|---|---|---|---|---|
| Sample No. | NCS Notation | Blackness/% | Chromaticness/% | Hue |
| Vivid Yellowish-green Sample 1 | S 0572-G18Y | 5 | 72 | Green 82%, yellow 18% |
| Vivid Yellowish-green Sample 2 | S 0675-G20Y | 6 | 75 | Green 80%, yellow 20% |
| Spicy Green Sample 1 | S 3361-G | 33 | 61 | Pure green |
| Spinach Green Sample 1 | S 4251-G | 42 | 51 | Pure green |
| Spinach Green Sample 2 | S 5143-B93G | 51 | 43 | Green 93%, blue 7% |
| Apple Green Sample 1 | S 1161-G | 11 | 61 | Pure green |
| Dark Green Sample 1 | S 8506-B95G | 85 | 6 | Green 95%, blue 5% |
| Green Sample 1 | S 5636-G29Y | 56 | 36 | Green 71%, yellow 29% |
| White Sample 1 | S 0507-R84B | 5 | 7 | Blue 84%, red 16% |
| White Sample 2 | S 0505-G | 5 | 5 | Pure green |
| Yellow Sample 1 | S 2463-Y | 24 | 63 | Pure yellow |
| Yellow Sample 2 | S 3360-Y6R | 33 | 60 | Yellow 94%, red 6% |
| Red Sample 1 | S 3558-Y73R | 35 | 58 | Red 73%, yellow 27% |
| Purple Sample 1 | S 3132-R41B | 31 | 32 | Red 59%, blue 41% |
| Purple Sample 2 | S 5330-R62B | 53 | 30 | Blue 62%, red 38% |
| Purple Sample 3 | S 2230-R30B | 22 | 30 | Red 70%, blue 30% |

3) Calculate the hue-purity, color-strength and relative chromaticity of the color of the samples according to the blackness, chromaticness, and hue. Wherein, hue-purity is x % the secondary psychological primary color to the main psychological primary color, wherein x % is the percentage proportion of the secondary psychological primary color in the hue; color-strength=blackness+chromaticness; relative chromaticity=chromaticness/color-strength. See the results in Table 2 (due to the huge amount of data, Table 2 only lists the calculation results of the quality indexes of the colors in Table 1).

TABLE 2

| | Color Quality Indexes | | | Compared to the typical quality characteristics in people's common sense and experience |
|---|---|---|---|---|
| Sample No. | Hue-purity | Color-strength/% | Relative chromaticity/% | |
| Vivid Yellowish green Sample 1 | 18% yellow to Green | 77 | 93.5 | Vivid yellowish green with moderate strength |
| Vivid Yellowish green Sample 2 | 20% yellow to Green | 81 | 92.6 | |
| Spicy Green Sample 1 | 100% Green | 94 | 64.9 | Pure green similar to pepper |
| Spinach Green Sample 1 | 100% Green | 93 | 54.8 | Dull green similar to spinach |
| Spinach Green Sample 2 | 7% blue to Green | 94 | 45.7 | |
| Apple Green Sample 1 | 100% Green | 72 | 84.7 | Light green similar to green apple |
| Dark Green Sample 1 | 5% blue to Green | 91 | 7.0 | Dark green similar to black |
| Green Sample 1 | 29% yellow to Green | 92 | 39.1 | Yellowish and grayish green |

TABLE 2-continued

| Sample No. | Color Quality Indexes | | | Compared to the typical quality characteristics in people's common sense and experience |
|---|---|---|---|---|
| | Hue-purity | Color-strength/% | Relative chromaticity/% | |
| White Sample 1 | 16% red to Blue | 12 | 58.3 | Color is very light, little significance for the test of hue-purity and relative chromaticity |
| White Sample 2 | 100% Green | 10 | 50 | Color is very light, little significance for the test of hue-purity and relative chromaticity |
| Yellow Sample 1 | 100% Yellow | 87 | 72.4 | Khaki |
| Yellow Sample 2 | 6% red Yellow | 93 | 64.5 | Khaki with a little bit of orange |
| Red Sample 1 | 27% yellow to Red | 93 | 62.4 | Maroon |
| Purple Sample 1 | 41% blue to Red | 63 | 50.8 | Purple with moderate color-strength |
| Purple | 38% red | 83 | 36.1 | Bluish purple |
| Sample 2 Purple Sample 3 | to Blue 30% blue to Red | 52 | 57.7 | Light pinkish purple |

In Table 2, we can also use the transitional intermediate color as a reference to calculate and indicate the hue-purity. The calculation method is: Hue-purity is y % the main psychological primary color to the transitional intermediate color, wherein y % is half of the difference between the percentage proportion of the main psychological primary color in the hue and the percentage proportion of the secondary psychological primary color in the hue. So the hue-purity of Yellow Sample 2, Red Sample 1, Purple Sample 1, Purple Sample 2, and Purple Sample 3 can be indicated in turn as: 44% yellow to Orange, 23% red to Orange, 9% red to Purple, 12% blue to Purple, and 20% red to Purple.

4) After the analysis, statistics and calibration of the index parameters of all the colors in the training set, we then identify, classify, quantity and define the specific colors represented by the samples, according to the quantified hue-purity, color-strength and relative chromaticity. Each color is defined in Table 3 (due to the huge amount of data, Table 3 only lists definitions of some typical colors)

TABLE 3

| Color-strength Hue-purity | Color-strength/% | | | | |
|---|---|---|---|---|---|
| | Color-strength ≥90 (can be defined as "extremely strong") | 90> Color-strength ≥81 (can be defined as "very strong") | 81> Color-strength ≥60 (can be defined as "strong") | 60> Color-strength ≥40 (can be defined as "weak") | Color-strength <40 (can be defined as "very weak") |
| 10%~20% (contains) yellow to Green | relative chromaticity ≥60: yellowish green 6> relative chromaticity >15: — relative chromaticity ≤15: dark green | | relative chromaticity ≥60: vivid yellowish green relative chromaticity <60: — | | light green |
| 0 (contains)~10% (contains) yellow to Green | relative chromaticity ≥60: strong green 60> relative chromaticity ≥50: spicy green 50> relative chromaticity ≥15: spinach green relative chromaticity ≤15: dark green | | relative chromaticity ≥60: vivid green relative chromaticity ≤15: — | relative chromaticity ≥60: apple green relative chromaticity <60: — | |

TABLE 3-continued

| Color-strength Hue-purity | Color-strength ≥90 (can be defined as "extremely strong") | 90> Color-strength ≥81 (can be defined as "very strong") | 81> Color-strength ≥60 (can be defined as "strong") | 60> Color-strength ≥40 (can be defined as "weak") | Color-strength <40 (can be defined as "very weak") |
|---|---|---|---|---|---|
| 0~20% (contains) blue to Green | 5> relative chromaticity >15: — relative chromaticity ≤15: dark green | | relative chromaticity ≥50: bluish green relative chromaticity <50: — | | — |
| 10% (contains)~30% blue to Red | | relative chromaticity ≥50: reddish purple | | | relative chromaticity ≥50: pinkish purple |
| 30% (contains)~40% red to Blue | | | relative chromaticity <50: — Bluish purple | | |
| 30% (contains) blue to Red~30% red to Blue | | relative chromaticity ≥50: vivid purple 50> relative chromaticity ≥30: eggplant purple relative chromaticity <30: — | | | light purple |
| White | | Color-strength <15; the test of hue-purity and relative chromaticity may not be done | | | |

In Table 3, accurate quantitative definitions are given to the jadeite colors common to the market according to the hue-purity, color-strength and relative chromaticity. And the so-called "strong" degree of color-strength can match the "moderate strength" in people's common sense and experience in Table 2. Other undefined colors can be directly classified and named by hue according to the hue-purity, for example, the color whose hue-purity is 15% blue to green can be named as "bluish green". As purple is one of the typical colors of jadeite, the colors that contain a blue component and a red component can also be named as "purple", "reddish purple", or "bluish purple." When the color-strength is less than 15% (nearly pure white), all colors can be called white.

Example 2

Testing the color quality of unknown jadeites.

Step One: Use a NCS color scan to determine the blackness, chromaticness, and hue of the color of jadeite samples to be tested in a D50 standard illumination environment. The test results are shown in Table 4.

TABLE 4

| Sample No. | NCS Notation | Color Parameters | | |
|---|---|---|---|---|
| | | Blackness/% | Chromaticness/% | Hue |
| Unknown sample 1 | S 3848-B89G | 38 | 48 | Green 89%, blue 11% |
| Unknown sample 2 | S 2071-G19Y | 20 | 71 | Green 81%, yellow 19% |
| Unknown sample 3 | S 4133-G | 41 | 33 | Pure green |
| Unknown sample 4 | S 0542-G17Y | 5 | 42 | Green 83%, yellow 17% |

TABLE 4-continued

| Sample No. | NCS Notation | Color Parameters | | |
|---|---|---|---|---|
| | | Blackness/% | Chromaticness/% | Hue |
| Unknown sample 5 | S 5140-G10Y | 51 | 40 | Green 90%, yellow 10% |
| Unknown sample 6 | S 4230-R49B | 42 | 30 | Blue 51%, red 49% |
| Unknown sample 7 | S 4239-Y13R | 42 | 39 | Yellow 87%, red 13% |

Step Two: Calculate the hue-purity, color-strength and relative chromaticity of the color of the samples for testing the color quality of the samples. Identify, classify and name them according to the color definitions in Table 3 in Example 1. The test conclusions are shown in Table 5.

TABLE 5

| Sample No. | Color Quality Indexes | | | Test Conclusion |
|---|---|---|---|---|
| | Hue-purity | Color-strength/% | relative chromaticity/% | |
| Unknown sample 1 | 11% blue to Green | 86 | 55.8 | Bluish green |
| Unknown sample 2 | 19% yellow to Green | 91 | 78.0 | Yellowish green |
| Unknown sample 3 | 100% Green | 74 | 44.6 | Spinach green |
| Unknown sample 4 | 17% yellow to Green | 47 | 89.4 | Vivid yellowish green |
| Unknown sample 5 | 10% yellow to Green | 91 | 44.0 | Spinach green |

TABLE 5-continued

| Sample No. | Hue-purity | Color-strength/% | relative chromaticity/% | Test Conclusion |
|---|---|---|---|---|
| Unknown sample 6 | 49% red to Blue or indicated as 1% blue to Purple | 72 | 41.7 | Purple |
| Unknown sample 7 | 13% red to Yellow or indicated as 34% yellow to Orange | 81 | 48.1 | Yellowish orange |

Example 3

Use the method of testing the color quality of a colored gemstone provided in this application to identify the color quality of rubies suspected to be "pigeon's blood".

"Pigeon's blood" is a red considered to have the best quality and highest value with regard to rubies. As the old saying goes, "a little difference in color can lead to a big difference in price". Therefore, it is of great importance to use the method of testing the color quality of a colored gemstone provided in this application to identify "pigeon's blood".

First, collect a plurality of market-recognized rubies with the color of "pigeon's blood" as the training set, use a NCS color scan to determine the blackness, chromaticness, and hue of the samples in a D50 standard illumination environment, and calculate the hue-purity, color-strength and relative chromaticity of the "pigeon's blood". After the systematic analysis, statistics and correction, the quantitative definition of the "pigeon's blood" according to the hue-purity, color-strength and relative chromaticity is obtained as shown in the following Table 6:

TABLE 6

| Quality Index Color | Hue-purity | Color-strength/% | relative chromaticity/% | Typical quality characteristics |
|---|---|---|---|---|
| Pigeon's blood | 0 (contains)~15% (contains) yellow to Red | ≥90 | ≥85 | Extremely pure of the hue, extremely strong of the color-strength and the relative chromaticity. |

Identify the colors suspected "pigeon's blood". Calculate the quality indexes of the samples according to the color parameters determined by a NCS color scan in a D50 standard illumination environment, and match them with Table 6. The test conclusions are shown in Table 7.

TABLE 7

| Sample No. | Hue-purity | Color-strength/% | Relative chromaticity/% | Test Conclusion |
|---|---|---|---|---|
| Ruby sample 1 | 9% yellow to Red | 92 | 93.5 | pigeon's blood |
| Ruby sample 2 | 2% blue to Red | 90 | 94.4 | isn't pigeon's blood |
| Ruby sample 3 | 100% Red | 88 | 93.2 | isn't pigeon's blood |
| Ruby sample 4 | 16% yellow to Red | 93 | 89.2 | isn't pigeon's blood |
| Ruby sample 5 | 100% Red | 91 | 87.9 | pigeon's blood |
| Ruby sample 6 | 2% yellow to Red | 95 | 94.7 | pigeon's blood |

Match the index parameters in Table 7 with Table 6 and the following test conclusion can be obtained: In the six rubies, though sample 2, sample 3 and sample 4 are very similar to "pigeon's blood" in appearance, they cannot be identified as "pigeon's blood" as the hue-purity of sample 2 and sample 4 is not pure enough and the color-strength of sample 3 is not enough; Only sample 1, sample 5 and sample 6 can be truly identified as "pigeon's blood", and the color quality of sample 1, sample 5 and sample 6 from high to low is sample 6 (relative chromaticity 94.7%), sample 1 (relative chromaticity 93.5%) and then sample 5 (relative chromaticity 87.9%).

The above are further explanations of this application on the basis of specific preferred implementation embodiments, it cannot be deemed that the specific implementation of this application is only limited to these explanations. For technical staff in the field to which this application belongs, with the premise of not departing from the idea of this application, they can make a number of equivalents or obvious variations with the same performance or use, all these should be regarded as within the protection scope of this application.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A method of establishing a standard color library for a colored gemstone for testing the color quality of the colored gemstone, comprising: taking the color of the colored gemstone as an entirety visually composed of different color components, whose total amount of color components is constant, so as to calculate hue-purity, color-strength and relative chromaticity of said color to establish said standard color library for said colored gemstone, the steps are as follows:

(1) collecting a plurality of colored gemstone samples as a training set;
    (2) determining blackness, chromaticness, and hue of the color of said colored gemstone samples in said training set in a standard environment, wherein said color components include colored components and a white visual component, wherein said colored components include a black visual component and all chromatic visual components, wherein said blackness is the percentage content of said black visual component in said color of said colored gemstone, wherein said chromaticness is the percentage content of said chromatic visual components in said color of said colored gemstone;

(3) calculating said hue-purity, said color-strength and said relative chromaticity of said color of said colored gemstone samples according to said blackness, said chromaticness and said hue:

wherein said hue-purity represents the degree of purity or impurity and the offset color of said hue of said color of said colored gemstone calculated on the basis of one of four psychological primary colors and transitional intermediate colors;

wherein said four psychological primary colors are red, green, yellow and blue, wherein red and yellow, red and blue, yellow and green, green and blue are not opposed, there is a transitional intermediate color between two psychological primary colors which are not opposed; wherein said transitional intermediate colors are orange which between yellow and red, and purple which between red and blue;

when red and yellow, or, red and blue are detected in the color of colored gemstone samples, using one of the following two calculation methods: (a), hue-purity is x % the secondary psychological primary color to the main psychological primary color; and (b), hue-purity is y % the main psychological primary color to the transitional intermediate color; when green and blue, or, yellow and green are detected in the color of colored gemstone samples, the hue-purity is x % the secondary psychological primary color to the main psychological primary color;

wherein x % is the percentage proportion of the secondary psychological primary color in the hue, y % is half of the difference between the percentage proportion of the main psychological primary color in the hue and the percentage proportion of the secondary psychological primary color in the hue;

wherein: said main psychological primary color means the psychological primary color whose percentage proportion in said hue is more than 50%, and said secondary psychological primary color means the psychological primary color whose percentage proportion in said hue is less than 50%; when the percentage proportions of both psychological primary colors in said hue are 50%, then either of the psychological primary colors can be taken as said main psychological primary color, and the other can be taken as said secondary psychological primary color;

wherein said color-strength is as follows: color-strength=blackness+chromaticness;

wherein said relative chromaticity is as follows: relative chromaticity=chromaticness/color-strength; and (4) identifying, classifying, quantifying and defining the specific color represented by each colored gemstone sample in said training set according to said hue-purity, said color-strength and said relative chromaticity calculated in step (3) to get said standard color library for said colored gemstone.

2. The method of establishing a standard color library for a colored gemstone according to claim 1, wherein said blackness, said chromaticness and said hue are directly measured by using a color scan of the Natural Color System or determined by visual comparison between said colored gemstone samples and standard color cards of the Natural Color System.

3. The method of establishing a standard color library for a colored gemstone according to claim 1, wherein said blackness and said chromaticness are respectively equivalent to value B and value C determined by using the Ostwald Color System, and said hue is determined by using the Natural Color System.

4. The method of establishing a standard color library for a colored gemstone according to claim 1, wherein said standard environment is selected from one of a group composed of D50, D55 and D65 standard illumination environments.

5. The method of establishing a standard color library for a colored gemstone according to claim 2, wherein said standard environment is selected from one of a group composed of D50, D55 and D65 standard illumination environments.

6. The method of establishing a standard color library for a colored gemstone according to claim 3, wherein said standard environment is selected from one of a group composed of D50, D55 and D65 standard illumination environments.

7. The method of establishing a standard color library for a colored gemstone according to claim 1, wherein said identifying, classifying, quantifying and defining in said step (4) also includes using natural color nomenclature or said hue to name specific colors represented by said colored gemstone samples.

8. The method of establishing a standard color library for a colored gemstone according to claim 2, wherein said identifying, classifying, quantifying and defining in said step (4) also includes using natural color nomenclature or said hue to name specific colors represented by said colored gemstone samples.

9. The method of establishing a standard color library for a colored gemstone according to claim 3, wherein said identifying, classifying, quantifying and defining in said step (4) also includes using natural color nomenclature or said hue to name specific colors represented by said colored gemstone samples.

10. A method of testing the color quality of a colored gemstone, comprising: taking the color of the colored gemstone as an entirety visually composed of different color components, whose total amount of color components is constant, so as to calculate hue-purity, color-strength and relative chromaticity of said color to test said color quality of said colored gemstone, the steps are as follows:

(1) determining blackness, chromaticness, and hue of the color of said colored gemstone to be measured in a standard environment, wherein said color components include colored components and a white visual component, wherein said colored components include a black visual component and all chromatic visual components, wherein said blackness is the percentage content of said black visual component in said color of said colored gemstone, wherein said chromaticness is the percentage content of said chromatic visual components in said color of said colored gemstone;

(2) calculating said hue-purity, said color-strength and said relative chromaticity of said color of said colored gemstone to be tested according to said blackness, said chromaticness and said hue:

wherein said hue-purity represents the degree of purity or impurity and the offset color of said hue of said color of said colored gemstone calculated on the basis of one of four psychological primary colors and transitional intermediate colors;

wherein said four psychological primary colors are red, green, yellow and blue, wherein red and yellow, red and blue, yellow and green, green and blue are not opposed, there is a transitional intermediate color between two psychological primary colors which are not opposed; wherein said transitional intermediate colors are orange which between yellow and red, and purple which between red and blue;

when red and yellow, or, red and blue are detected in the color of colored gemstone samples, using one of the following two calculation methods: (a), hue-purity is x % the secondary psychological primary color to the main psychological primary color; and (b), hue-purity is y % the main psychological primary color to the transitional intermediate color; when green and blue, or, yellow and green are detected in the color of colored gemstone samples, the hue-purity is x % the secondary psychological primary color to the main psychological primary color;

wherein x % is the percentage proportion of the secondary psychological primary color in the hue, y % is half of the difference between the percentage proportion of the main psychological primary color in the hue and the percentage proportion of the secondary psychological primary color in the hue;

wherein: said main psychological primary color means the psychological primary color whose percentage proportion in said hue is more than 50%, and said secondary psychological primary color means the psychological primary color whose percentage proportion in said hue is less than 50%; when the percentage proportions of both psychological primary colors in said hue are 50%, then either of the psychological primary colors can be taken as said main psychological primary color, and the other can be taken as said secondary psychological primary color;

wherein said color-strength is as follows: color-strength=blackness+chromaticness;

wherein said relative chromaticity is as follows: relative chromaticity=chromaticness/color-strength; and (3) finding a matching color in a pre-established standard color library for this specific colored gemstone according to said method mentioned in claim 1 based on said hue-purity, said color-strength and said relative chromaticity calculated in step (2), and using the name of the matching color to indicate said color and said color quality of said colored gemstone to be tested.

11. The method of testing the color quality of a colored gemstone according to claim 10, wherein said blackness, said chromaticness and said hue are directly measured by using a color scan of the Natural Color System or determined by visual comparison between said colored gemstone sample and standard color cards of the Natural Color System.

12. The method of testing the color quality of a colored gemstone according to claim 10, wherein said blackness and said chromaticness are respectively equivalent to value B and value C determined by using the Ostwald Color System, and said hue is determined by using the Natural Color System.

13. The method of testing the color quality of a colored gemstone according to claim 10, wherein said standard environment is selected from one of a group composed of D50, D55 and D65 standard illumination environments.

14. The method of testing the color quality of a colored gemstone according to claim 11, wherein said standard environment is selected from one of a group composed of D50, D55 and D65 standard illumination environments.

15. The method of testing the color quality of a colored gemstone according to claim 12, wherein said standard environment is selected from one of a group composed of D50, D55 and D65 standard illumination environments.

* * * * *